United States Patent
Cabiri et al.

(10) Patent No.: US 8,783,518 B2
(45) Date of Patent: Jul. 22, 2014

(54) MULTIPLE-METERED SELF-CLEANING DISPENSER

(75) Inventors: Oz Cabiri, Maccabim-Reut (IL); Rodrigo Yelin, Zur-Yigal (IL); Ella Zlatkis, Mazkeret Batia (IL); Eran Eilat, Herzliya (IL)

(73) Assignee: Otic Pharma Ltd., Ariel (IL)

( * ) Notice: Subject to any disclaimer, the term of this patent is extended or adjusted under 35 U.S.C. 154(b) by 267 days.

(21) Appl. No.: 13/142,692

(22) PCT Filed: Dec. 27, 2009

(86) PCT No.: PCT/IL2009/001219
§ 371 (c)(1),
(2), (4) Date: Sep. 21, 2011

(87) PCT Pub. No.: WO2010/076786
PCT Pub. Date: Jul. 8, 2010

(65) Prior Publication Data
US 2012/0000931 A1    Jan. 5, 2012

Related U.S. Application Data

(60) Provisional application No. 61/141,002, filed on Dec. 29, 2008.

(51) Int. Cl.
*B65D 83/00*    (2006.01)
*B67D 1/08*    (2006.01)

(52) U.S. Cl.
USPC ............... 222/148; 222/402.2; 222/402.18

(58) Field of Classification Search
USPC ........... 222/402.1, 402.16, 402.17, 402.18, 222/402.2, 1, 129, 148, 149, 151, 190; 239/106, 112, 113
See application file for complete search history.

(56) References Cited

U.S. PATENT DOCUMENTS

| | | | |
|---|---|---|---|
| 3,185,356 A * | 5/1965 | Venns, Jr. ................ | 222/402.2 |
| 3,360,168 A * | 12/1967 | Bret ......................... | 222/335 |
| 3,497,112 A * | 2/1970 | Samuelson ............... | 222/148 |
| 3,527,388 A * | 9/1970 | Cooprider ................ | 222/635 |
| 3,583,606 A * | 6/1971 | Ewald ....................... | 222/402.18 |
| 3,628,733 A | 12/1971 | Kahn | |
| 3,767,125 A | 10/1973 | Gehres | |
| 3,878,973 A | 4/1975 | Riccio | |
| 4,033,487 A | 7/1977 | Micallef | |
| 5,085,351 A | 2/1992 | Martin | |
| 5,255,848 A | 10/1993 | Rhodehouse | |
| 5,897,093 A | 4/1999 | Le Derf | |

(Continued)

FOREIGN PATENT DOCUMENTS

| | | |
|---|---|---|
| DE | 202004015890 U1 | 2/2005 |
| EP | 0059143 A1 | 9/1982 |
| GB | 1260616 | 1/1972 |

*Primary Examiner* — Kevin P Shaver
*Assistant Examiner* — Stephanie E Williams
(74) *Attorney, Agent, or Firm* — Browdy and Neimark, PLLC

(57) ABSTRACT

A method for dispensing a plurality of metered doses of a fluid, comprising: providing a fluid in a container comprising a plurality of metering chambers and a plurality of tubes connectable to and movable relative to the chambers, wherein the tubes are externally open or open to the fluid; connecting to the chambers tubes open to the fluid, thereby loading the chambers with fluid; and selectively connecting one or more externally open tubes to one or more chambers, thereby dispensing the fluid contents of the one or more chambers via an external opening.

20 Claims, 10 Drawing Sheets

(56) References Cited

U.S. PATENT DOCUMENTS

| | | |
|---|---|---|
| 6,158,674 A | 12/2000 | Humphreys |
| 6,257,457 B1 | 7/2001 | Oechsel |
| 6,290,217 B1 | 9/2001 | Schneider |
| 6,406,011 B1 | 6/2002 | Kosar |
| 6,634,570 B2 | 10/2003 | Scherer |
| 6,702,155 B1 | 3/2004 | Rebne |
| 7,727,549 B2 | 6/2010 | Kabra |
| 2006/0030509 A1 | 2/2006 | Modi |

* cited by examiner

Idle - loading

Dose

Extended dose

Cleaning

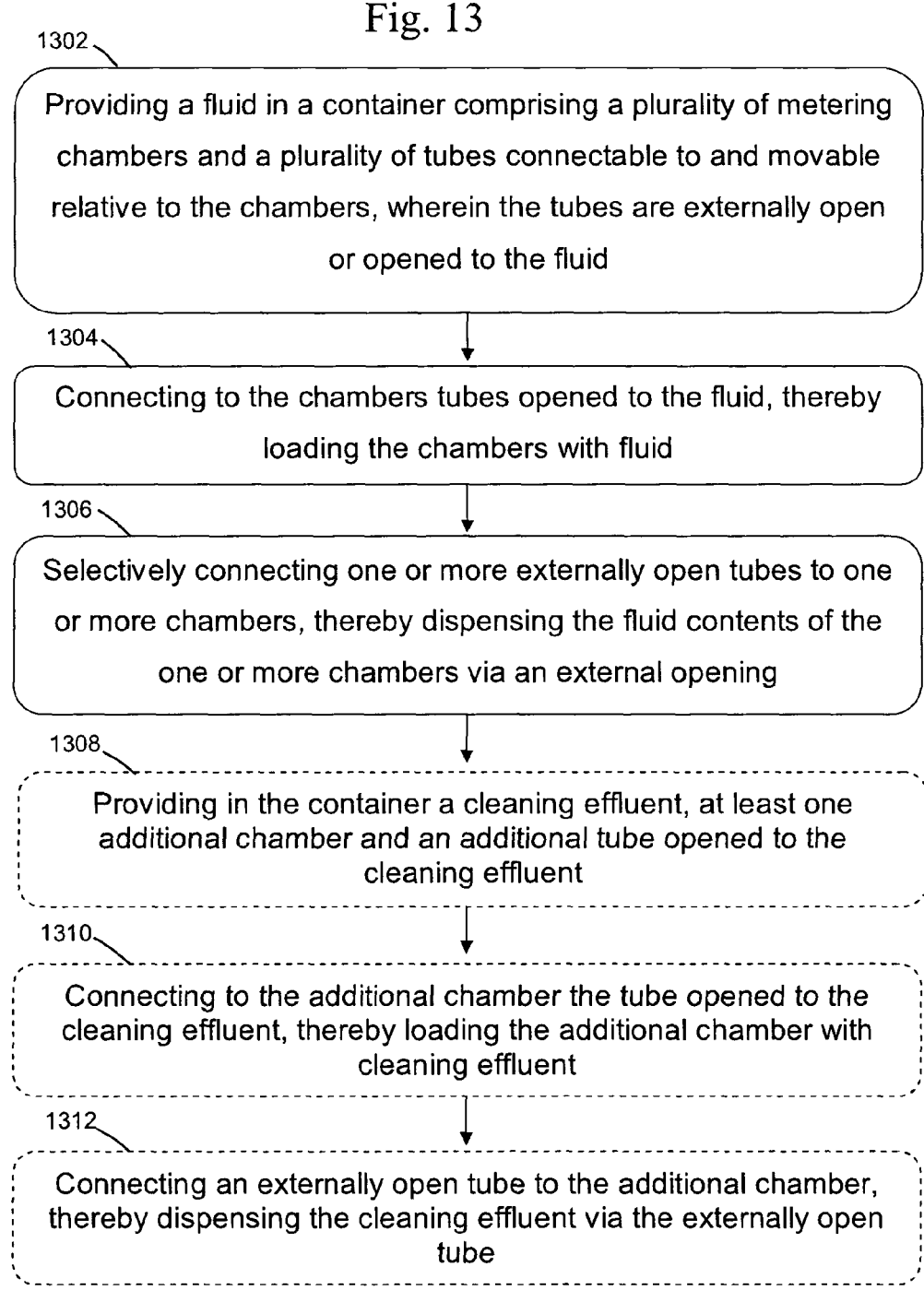

MULTIPLE-METERED SELF-CLEANING DISPENSER

RELATED APPLICATION

This application is corresponds to PCT/IL2009/001219, filed Dec. 27, 2009, which claims the benefit of U.S. Provisional Application No. 61/141,002, filed Dec. 29, 2008, the subject matter, of which is incorporated herein by reference in their entirety.

FIELD OF THE INVENTION

The invention generally relates to fluid dispensers. Some embodiments of the invention relate to apparatus and methods for dispensing preset quantities, wherein some embodiments further relate to self-cleaning dispensers.

BACKGROUND OF THE INVENTION

Fluid dispensers are commonly found in household or engineering applications such as perfume bottles, cosmetic foams, pharmaceuticals, disinfectant or oil or paint dispensers or others such as aerosol canisters.

Typically a fluid in a container is pushed out due to a pressurized propellant such as a gas pre-filled or pumped into the container, or the fluid is drawn out by a pump or a squeeze.

In some ordinary cases the dispensers have a continuous operation, that is, as long as a release valve is activated the fluid is expelled. In other cases the dispensers operation is intermittent, that is, some volume is delivered in a manner responsive to pumping or squeezing.

In some applications, for example therapeutical applications, the dispensed quantity or volume of the fluid has to be controlled. Various mechanisms were proposed for delivering fixed or variable controlled quantities. For example, U.S. Pat. No. 3,878,973 relates to a piston-cylinder with a metering valve, U.S. Pat. No. 6,702,155 that relates to metering a dose by a plunger operated by a wheel, U.S. Pat. No. 4,033,487 that relates to a dispenser with double-handled trigger where each handle releases a pre-set dose, U.S. Pat. No. 6,257,457 that relates to a device for spraying fluid in a tank with a fractioning means to fraction the fluid into doses, or U.S. Pat. No. 5,085,351 that relates to releasing an predetermined quantity from a pressurized reservoir.

Generally, in a dual or multiple metered doses dispenser, the user has to perform some special operation in order to select between two or more doses or to set the dose to be released. For example, pressing different triggers or rotating a wheel, may require maneuvering the position of the container, the hands or the fingers.

Typically fluid is delivered out of a dispenser via a narrow outlet such as a nozzle. Often, after dispensing a fluid, some fluid residues remain in the nozzle and may dry out or otherwise change, resulting in clogging or obstructing the passage of fluid in and out of the nozzle. Some mechanisms were proposed for cleaning a nozzle. For example, U.S. Pat. No. 5,255,848 relates to a multiple orifice spray nozzle having reversible orifice cleaning, U.S. Pat. No. 6,634,570 that relates to a needle that pushes into the nozzle under spring force, or US 2006/0030509 that relates to exchanging the fluid container with a cleaner container to release the cleaner fluid via the nozzle.

SUMMARY OF THE INVENTION

An aspect of some embodiments of the invention provides apparatus and methods for dispensing, via an outlet of a container holding a fluid, a plurality of controlled doses of the fluid by a plurality of tubes which selectively connect and disconnect chambers within the container according to the position of the tubes in the dispenser. The selective connections effect loading the chambers with the fluid and a subsequent discharge thereof.

Typically, the tubes, or at least a subset thereof, operate in unison with each other. Preferably, the tubes are constructed as a multi-lumen rod.

Another aspect of some embodiments of the invention relates to an apparatus and method for automatic post self-cleaning of an outlet of a fluid dispensing container by a cleaning effluent. The cleaning is facilitated by a tube which selectively connects and disconnects at least one chamber within the container with the cleaning effluent according to the position of the tube in the container such that the effluent is automatically discharged subsequent to dispensing a dose of fluid.

Typically, the tube operates in unison with the tubes used for dispensing the fluid. Preferably, the tube is formed as a lumen in a multi-lumen rod used for dispensing fluid.

In some embodiments, the post cleaning is intended for mechanical cleaning of an outlet of the dispensing container, such as sweeping away residues by an effluent flow. Optionally or additionally, the cleaning provides a substance to react with the dispensed substance or a modified form thereof, thereby effecting removal, inactivation, dissolving or disintegration thereof.

In some embodiments of the invention, the cleaning effluent is a gas contained in the fluid container, such as a propellant gas. Optionally, the fluid substantially comprises a condensed phase of the propellant gas, possibly with some additives.

Yet another aspect of some embodiments of the invention relates to a kit comprising components for assembling dose dispensing and/or cleaning structures and/or mechanisms to be installed in a container to provide a dispenser.

In some embodiments of the invention, the structure and/or mechanism for fluid dispensing and/or self-cleaning is simple or plain, at least relative to the structure and/or mechanism of some other multi-dose and/or self-cleaning dispensers known in the art. Optionally, the structure and mechanism fit into existing containers or bottles, possibly by providing a suitable lid or modifying the design or structure of an existing lid.

A potential operational advantage of dispensers according to some embodiments of the invention is that no maneuvering or changing the position of the dispenser and/or the hands and/or the fingers is required in order to discharge a particular dose or doses or self-cleaning.

Similarly, the same operation is used for dispensing doses for different applications or cases. For example, in ear treatment by pushing weakly on a release button of a dispenser a small (e.g. single) dose of foam with medication is administered to a child's ear, while by a stronger push a larger dose (e.g. a plurality of doses) is administered to an adult.

According to an aspect of some embodiments of the present invention there is provided a method for dispensing a plurality of metered doses of a fluid, comprising:

(a) providing a fluid in a container comprising a plurality of metering chambers and a plurality of tubes connectable to and movable relative to the chambers;

(b) connecting to the chambers tubes open to the fluid, thereby loading the chambers with fluid; and (c) selectively connecting one or more externally open tubes to one or more chambers, thereby dispensing the fluid contents of the one or more chambers via an external opening.

In some embodiments, connectable to the chambers comprises having holes at planned positions on the tubes, selectively providing or preventing a passage between a tube and a chamber.

In some embodiments, selectively connecting comprises moving tubes to a position where a particular chamber is connected to an externally open tube while concurrently disconnecting the particular chamber from a tube open to the fluid.

In some embodiments, selectively connecting comprises moving tubes to a position where particular chambers are connected to externally open tubes while concurrently disconnecting the particular chambers from tubes open to the fluid.

In some embodiments, selectively connecting comprises progressively moving tubes to consecutive positions, successively connecting particular chambers to externally open tubes while concurrently disconnecting the particular chambers from tubes open to the fluid.

In some embodiments, dispensing the fluid contents comprises at least one of a liquid, gas, spray, foam, solution, suspension, emulsion, gel, colloid, powder, microparticles, cream, lotion or paste form, or a combination thereof.

In some embodiments, providing a fluid in a container comprises providing a fluid pressurized by a pressure greater than the ambient pressure outside the container.

In some embodiments, the method further comprises:

(a) providing in the container a cleaning effluent, at least one additional chamber and an additional movable tube open to the cleaning effluent;

(b) connecting to the additional chamber the tube open to the cleaning effluent, thereby loading the additional chamber with cleaning effluent; and (c) connecting an externally open tube to the additional chamber, thereby dispensing the cleaning effluent via the externally open tube.

In some embodiments, connecting externally open tube to the additional chamber comprises moving tubes to a position where the additional chamber is connected to an externally open tube while synchronously disconnecting the additional chamber from the tube open to the cleaning effluent.

In some embodiments, connecting externally open tube to the additional chamber is facilitated subsequently to dispensing a fluid from at least one other chamber.

In some embodiments, a tube open to the cleaning effluent comprises a tube connected to a further provided auxiliary chamber open to the cleaning effluent.

In some embodiments, providing an effluent comprises providing a gas at a pressure greater than the ambient pressure outside the container In some embodiments, providing an effluent comprises providing a fluid alterable to a cleaning effluent.

According to an aspect of some embodiments of the present invention there is provided an apparatus for dispensing a plurality of metered doses of a fluid, comprising:

(a) a container fillable with a fluid to at least a portion of the container;

(b) a plurality of chambers disposed in the container;

(c) a plurality of tubes open to said portion, connectable to and movable relative to the chambers, providing selectable connections between said portion and the chambers for loading the fluid to the chambers; and (d) a plurality of externally open tubes connectable to and movable relative to the chambers, providing a selectable external connection to at least one chamber for dispensing the content of the at least one chamber.

In some embodiments, connectable to the chambers comprises having holes at planned positions on the tubes, selectively providing or preventing a passage between a tube and a chamber.

In some embodiments, the apparatus is structured to effect a mutual exclusiveness of (i) providing connections between said portion and the chambers and (ii) providing an external connection to at least one chamber.

In some embodiments, the apparatus further comprises:

(a) at least one additional chamber, disposed in the container, connectable to an externally open tube; and (b) at least one additional tube, open to the container outside of said portion, connectable to and movable relative to the additional chamber and allowing a selectable connection between the additional chamber and outside of said portion for loading into the additional chamber a provided cleaning effluent for a subsequent discharge via the externally open tube.

In some embodiments, the cleaning effluent is fillable from outside of said portion.

In some embodiments, at least a portion of the tubes are packed into a group.

In some embodiments, at least a portion of the tubes are formed as lumens in a stem.

In some embodiments, the externally open tubes are connected to an outlet.

According to an aspect of some embodiments of the present invention there is provided an apparatus for cleaning an outlet of a fluid dispensing container, comprising:

(a) a cavity having a volume fillable with a cleaning effluent;

(b) at least one chamber disposed in the container;

(c) an externally open tube connectable to and movable relative to the chamber; and (d) an additional tube open to the volume and connectable to and movable relative to the chamber, providing a selectable connection between the chamber and the volume for loading into the chamber a provided cleaning effluent for a subsequent discharge via the externally open tube.

In some embodiments, dispensing a fluid from the container effects a connection between the chamber and the volume by the additional tube thereby loading the chamber with the cleaning effluent.

In some embodiments, the externally open tube is connectable to a chamber loaded with the cleaning effluent subsequent to dispensing a fluid.

In some embodiments, the cavity constitutes a part of the container.

In some embodiments, the cavity constitutes at least a part of an additional container.

In some embodiments, the tubes are formed as lumens in a stem.

According to an aspect of some embodiments of the present invention there is provided a kit for assembling a structure for dispensing a plurality of metered doses of a fluid, comprising:

(a) a plurality of chambers or part thereof; and (b) a plurality of tubes formed to move relative to the chambers and provide selectable connections with the chambers.

In some embodiments, the tubes are formed as lumens in a stem.

In some embodiments, the chambers constitute an assembly.

In some embodiments, the chambers and tubes constitute an assembly of chambers and movable tubes therein.

In some embodiments, the chambers and tubes constitute an assembly of chambers and a movable stem having a plurality of lumens.

In some embodiments, the kit further comprises a can for disposing the chambers and tubes therein.

In some embodiments, the kit further comprises at least one fluid for dispensing.

In some embodiments, the kit further comprises instructions for using the kit.

In the specification and claims the following terms and derivatives thereof imply the respective non-limiting characterizations below.

Dispenser/dispensing—a container (a can, canister, bottle, flask, bag) holding one or more fluids and having an outlet opening externally of the container for releasing a fluid by a mechanism disposed in the container, wherein releasing comprises or denotes emitting, ejecting or discharging the fluid outside the container, collectively referred to as dispensing.

Fluid—at least one of a liquid, gas, aerosol, foam, while not precluding powder (e.g. microparticles or microcapsules), emulsion, gel, colloid, cream, lotion, paste or a mixture and/or combination thereof, and optionally comprising a volatile constituent. A fluid is also denoted as 'effluent' such as to resolve ambiguity when two fluids are referred to.

Cleaning effluent—fluid (e.g. a gas) that removes, at least partially, residues of a fluid from a nozzle and/or a tube.

Cleaning/Post-cleaning—discharging a cleaning fluid (effluent), where post-cleaning is subsequent to discharging a dose of fluid from a dispenser.

Outlet (of a dispenser)—one or more tubes, such as a nozzle or nozzles, opening externally of the dispenser, optionally with intermediate tube or tubes connecting to the dispenser or a part or a hollow thereof.

Externally open/opening—having a direct or indirect opening or passage to outside of a container.

Lumen—a cavity, typically having a longitudinal dimension larger than other dimensions perpendicular thereto, such the cavity of a tube.

Stem—an elongated part having a length (e.g. pole, rod, shaft) and having one or more lumens along at least part of the length thereof, such as cavities formed in a shaft or such as a pack of tubes.

Pressure (pressurized)—a pressure larger than atmospheric (or ambient pressure). For example, about 5 Atm, or any pressure effective to discharge out of a dispenser a fluid stored therein.

Metered/controlled dose—a defined or pre-set amount of a substance, such as a known volume of a fluid.

Opening/open (regarding a hollow such as tube)—having access for fluid, either directly or indirectly such as via another tube or passage.

Connect—provide or possess a direct or indirect passage for a fluid between two or more hollows, such as between a tube and a chamber; Disconnect—lacking or preventing passage for a fluid.

Without limiting, the terms 'container' and 'canister' are used interchangeably, the terms 'tube' and 'lumen' are used interchangeably, and the terms 'nozzle' and 'outlet' are used interchangeably, and do not preclude a plurality thereof.

BRIEF DESCRIPTION OF THE DRAWINGS

The invention may be understood upon reading of the following detailed description of non-limiting exemplary embodiments thereof, with reference to the following drawings.

Identical or duplicate or equivalent or similar structures, elements, or parts that appear in more than one drawing are generally labeled with the same reference numeral, optionally with an additional letter or letters for reference to particular objects. Duplicate or equivalent or similar parts may not be repeatedly labeled and/or described. Dimensions of components and features shown in the figures are chosen for convenience or clarity of presentation and are not necessarily shown to scale or true perspective. For convenience of clarity, some elements or structures are not shown or shown only partially and/or with different perspective.

FIG. 13 schematically illustrates a flowchart outlining actions for dispensing a plurality of metered doses of a fluid with optional cleaning, according to exemplary embodiments of the invention.

DESCRIPTION OF EMBODIMENTS OF THE INVENTION

Figure 1:
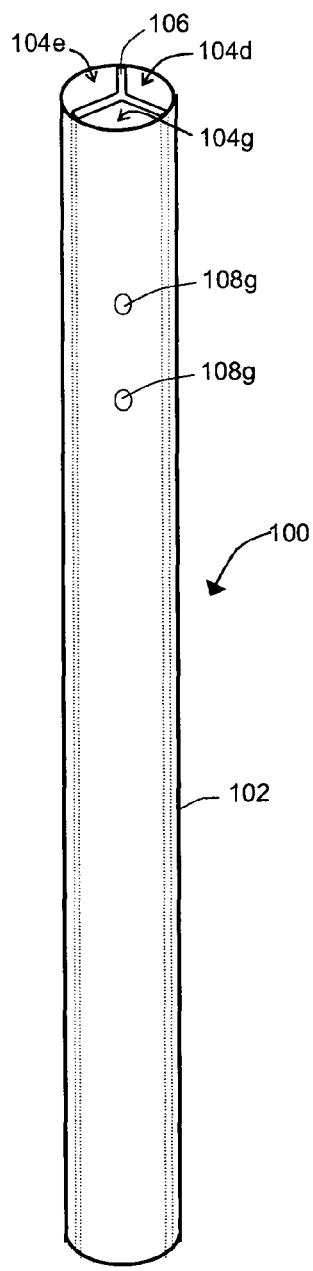
FIG. 1 schematically illustrates a stem having three lumens, according to exemplary embodiments of the invention.

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

The non-limiting section headings used herein are intended for convenience only and should not be construed as limiting the scope of the invention.

General Terminology

In the specification and claims, unless otherwise specified, the terms 'preferred', 'preferably', 'typical' or 'typically' and their inflections and conjugates do not limit the scope of the invention or embodiments thereof.

In the specification and claims, unless otherwise specified, the terms 'comprises', 'comprising', 'includes', 'including', 'having' and their inflections and conjugates denote 'including but not limited to'.

The term 'may' denotes an option which is either or not included and/or used and/or implemented, yet the option constitutes at least a part of some embodiments of the invention without limiting the scope thereof.

In the specification and claims, unless otherwise specified, referring to an object with an indefinite singular article (e.g. "a thing") does not preclude a reference to a plurality thereof (e.g. "things"), and the term 'plurality' refers to two or more entities.

When a range of values is recited, it is merely for convenience or brevity and includes all the possible sub-ranges as well as individual numerical values within that range. Any numeric value, unless otherwise specified, includes also practical close values enabling an embodiment or a method, and integral values do not exclude fractional values.

Overview

Without limiting generality and the scope of the invention, the description that follow relates to three tubes arranged in a triple-lumen rod moving inside four successive chambers. Two chambers define volumes of two doses and the other two chambers are used for gas buffering and storage for post-cleaning. The tubes, or lumens, are not continuous and comprise internal stoppers or separators (e.g. internal planes, membranes) separating or isolating sections of the tubes. Additionally, the tubes have openings (holes, perforations) on sides thereof for connections between chambers.

Adding more dose chambers, together with corresponding additional tubes (or lumens) a larger number of controlled doses, or different combinations of doses, can be delivered using the same mechanism and/or procedure.

The mechanism for controlled dose delivery operation and for automatic post-cleaning operation share some common principles and elements, yet each operation can be implemented separately independent of each other, as can be recognized by the discussions further below. However, to avoid superfluous description, without limiting, both operations are generally discussed together.

For brevity and clarity and without limiting, when deemed inessential for the description below, reference will be made to a tube or a lumen disregarding internal discontinuities or to two or more consecutive tubes or lumens.

It should be emphasized that relating to multi-lumen rod is used as a non-limiting example and other variations or combinations of lumens or tubes may be used.

Components

FIG. 1 schematically illustrates a stem 100 comprising a sleeve 102 having an internal hollow and a divider 106 dividing the interior of sleeve 102 into three lumens 104, designated as 104g ('g' for gas), 104d ('d' for dose) and 104e ('e' for extended dose). Lumens 104 have holes 108, shown as 108g in lumen 104g (and hidden for the other lumens).

Figure 2:
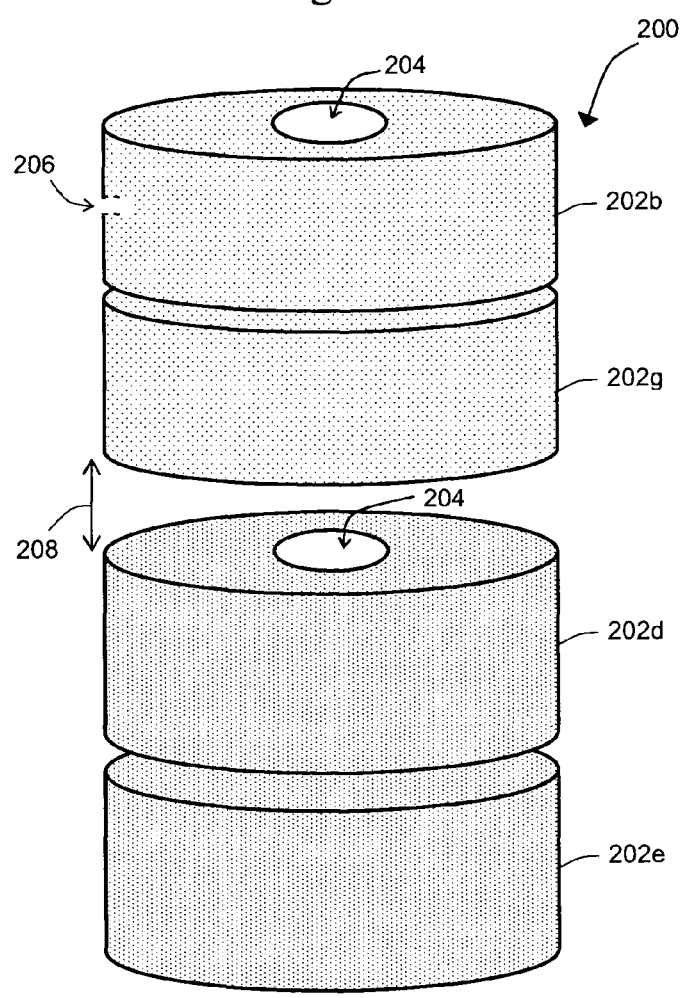
FIG. 2 schematically illustrates an assembly comprising two chambers for post cleaning by gas and two chambers for fluid dose dispensing, according to exemplary embodiments of the invention.

FIG. 2 schematically illustrates an assembly 200 comprising four chambers 202. Two chambers, 202b and 202g, are used for gas buffering and storage for post cleaning, respectively, where chamber 202b has an opening 206. The other two chambers, 202d and 202e, are used for dose and extended dose fluid dispensing, respectively. A chamber 202 adjoins another chamber 202, or a chamber 202 is separated from another chamber 202 by a distance such as 208, according to the mutual operation with stem 100, as described below.

The meaning of the designations (subscripts) such as 'b', 'g', 'd' and 'e' can be appreciated according to the description further below.

Assembly 200 is, eventually, disposed in a dispenser canister such as depicted as canister 440 in FIG. 4 discussed below.

Figure 3:
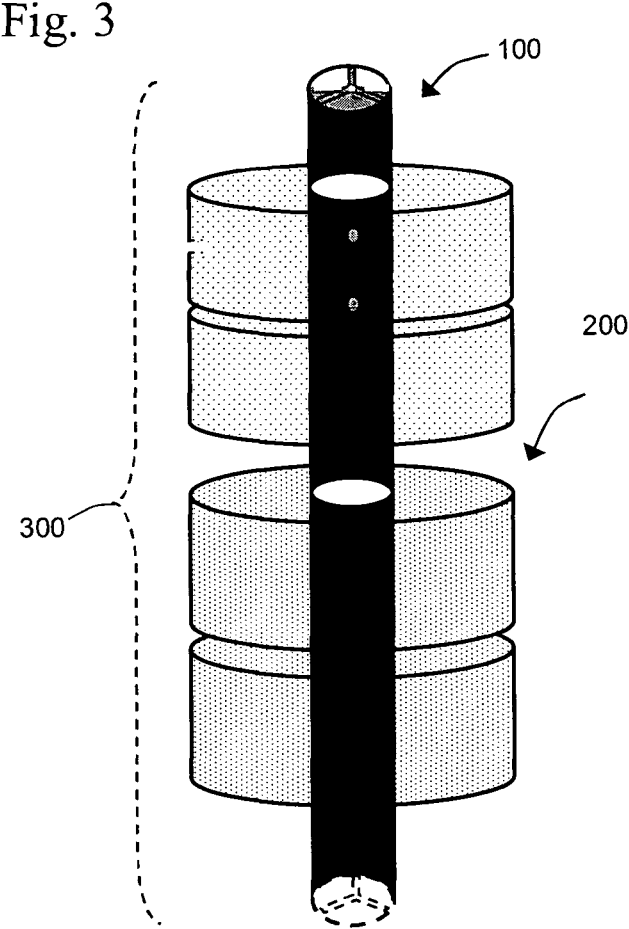
FIG. 3 schematically illustrates a combination of a stem and chambers assembly, according to exemplary embodiments of the invention.

Chambers 202 have hollows therein successively forming a passage 204 (shown in 202b and 202d) for insertion and movement of stem 100, as illustrated in FIG. 3 that shows a structured combination (also a mechanism) 300 where stem 100 is disposed in passage 204 in chambers assembly 200. In some embodiments, using suitable materials, the diameters (or other cross-sections) of stem 100 and passage 204 fit and tighten to each other while allowing a movement of stem 100 in passage 204. Optionally or alternatively, some sealing element or elements and/or sealants and/or lubricants are used to allow movement of stem 100 along passage 204.

Figure 4:
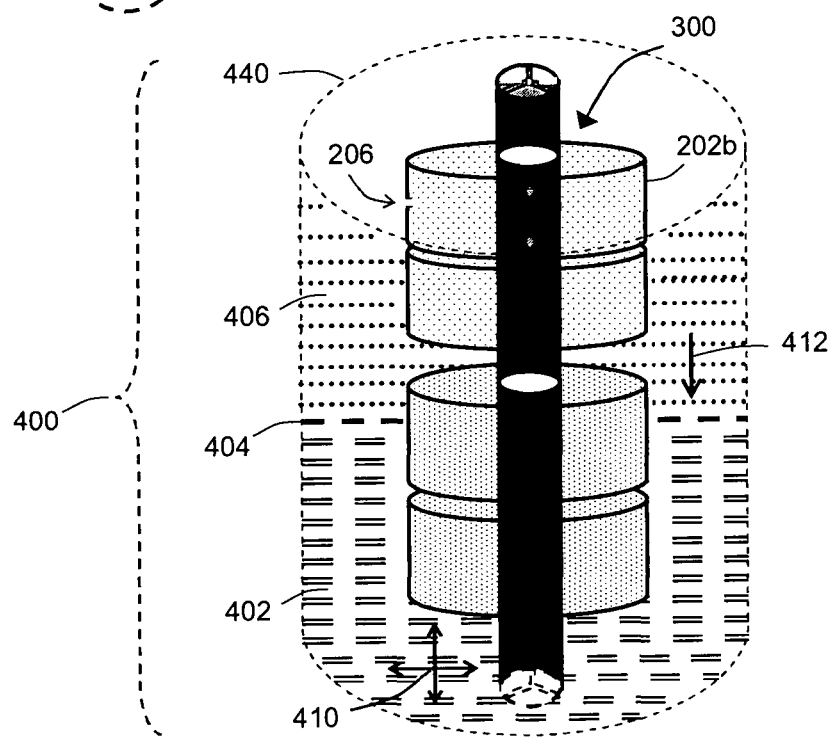
FIG. 4 schematically illustrates a combination of a stem and chambers assembly disposed in a dispenser canister, according to exemplary embodiments of the invention.

As illustrated in FIG. 4, combination 300 comprising stem 100 and chambers 200 (hereinafter 'dispensing gear' or 'gear') is, eventually, disposed in a canister, figuratively depicted as canister 440. In typical cases or embodiments of the inventions, canister 440 is sealed about stem 100 that movably protrudes outside thereof. In typical cases or embodiments of the inventions, canister 440 is at least partially filled with a fluid 402 up to a level 404 (a filled portion) and with pressurized gas (e.g. propellant) shown as 406 above level 404 (a section volume). Gas 406 imparts pressure on fluid 402 as indicated by arrow 412, thereby applying a hydrostatic pressure in fluid 402 as schematically indicated by arrows 410. Canister 440 with gear 300 therein, optionally with auxiliary elements such as a nozzle (not shown), is referred to as a dispenser 400.

In some embodiments of the invention, fluid 402 and gas 406 comprise a composition in a pressurized two-phase system in equilibrium, namely a condensed phase such as liquid and a gaseous phase, respectively. Optionally, fluid 402 comprises additional ingredients, such as food, medications, surfactants or lubricants or other additives, optionally in the form of a solution, suspension, emulsion, gel, colloid, powder, microparticles, microcapsules, cream, lotion or paste, or a combination thereof, according to the objective and/or application and/or intended function of the dispensed material. In some embodiments, the microparticles or microcapsules (e.g. about or less than about 100 µm) comprise a medication, wherein the microparticles are coated and/or mixed with another material such as for effecting a slow release of the medication or as a lubricant or for proper adhesion to the intended location or for preservation of the medication (or any other active constituent).

Figure 5:
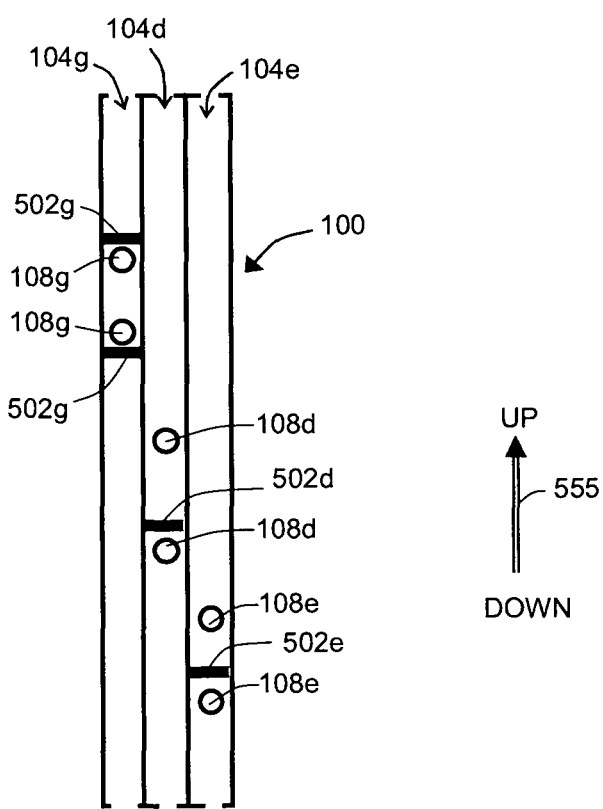
FIG. 5 schematically illustrates structures of lumens in a stem, according to exemplary embodiments of the invention.

FIG. 5 schematically illustrates a figurative arrangement of lumens 104 in stem 100, or alternatively and equivalently as separate tubes joined or packed or bundled together. For convenience, a typical (at least approximately) orientation of 'up' direction is indicated by an arrow 555.

Lumen 104g has two holes (openings) 108g in a region isolated between upper and lower stoppers 502g. Lumen 104d has two holes 108d, separated by a stopper 502d. Lumen 104e has two holes 108e separated by a stopper 502e. The basis and justification for the number of holes and stoppers and the positions of the holes and the stoppers in the lumens and with respects to chambers 202 may be recognized as the operation of gear 300 is described with further reference to FIG. 6.

It should be noted, however, that the upper and lower parts of lumens 104*d* or 104*e* (above and below stoppers 502*d* or 502*e*, respectively) may be considered and/or constructed as two separate tubes each closed at one end, wherein an upper part is externally open (to the external environment) and a lower part is open to the fluid. Also, the section between stoppers 502*g* may be formed regardless of lumen 104*g* and optionally attached to one or more of lumens 104*d* or 104*e*.

Exemplary Operation

With additional reference to FIGS. 1-5, FIG. 6 schematically illustrates some stages in an operation of a triple-lumen stem 100 with an assembly 200 of chambers 202 inside canister 440 containing a fluid as a liquefied propellant gas. For further clarification, FIG. 7A-D show cross-sectional depth views of some stages corresponding to stages illustrated in FIG. 6.

Gear 300, namely, lumens 104 and chambers 202, is assumed to be disposed in dispenser 400 with canister 440 enclosing fluid 402 under pressure of gas 406 as described with respect to FIG. 4. Buffer chamber 202*b* is above fluid level 404 and opened to gas 406 via opening 206. Lower parts of lumens 104*d* and 104*e* of stem 100 (or equivalent tubes) have openings in or accessible to fluid 402. Upper parts of lumens 104*d* and 104*e* of stem 100 (or equivalent tubes) have openings external to the dispenser either directly or indirectly—for example, via an outlet structure such as a nozzle with an optional intermediate tubing.

Figure 6:
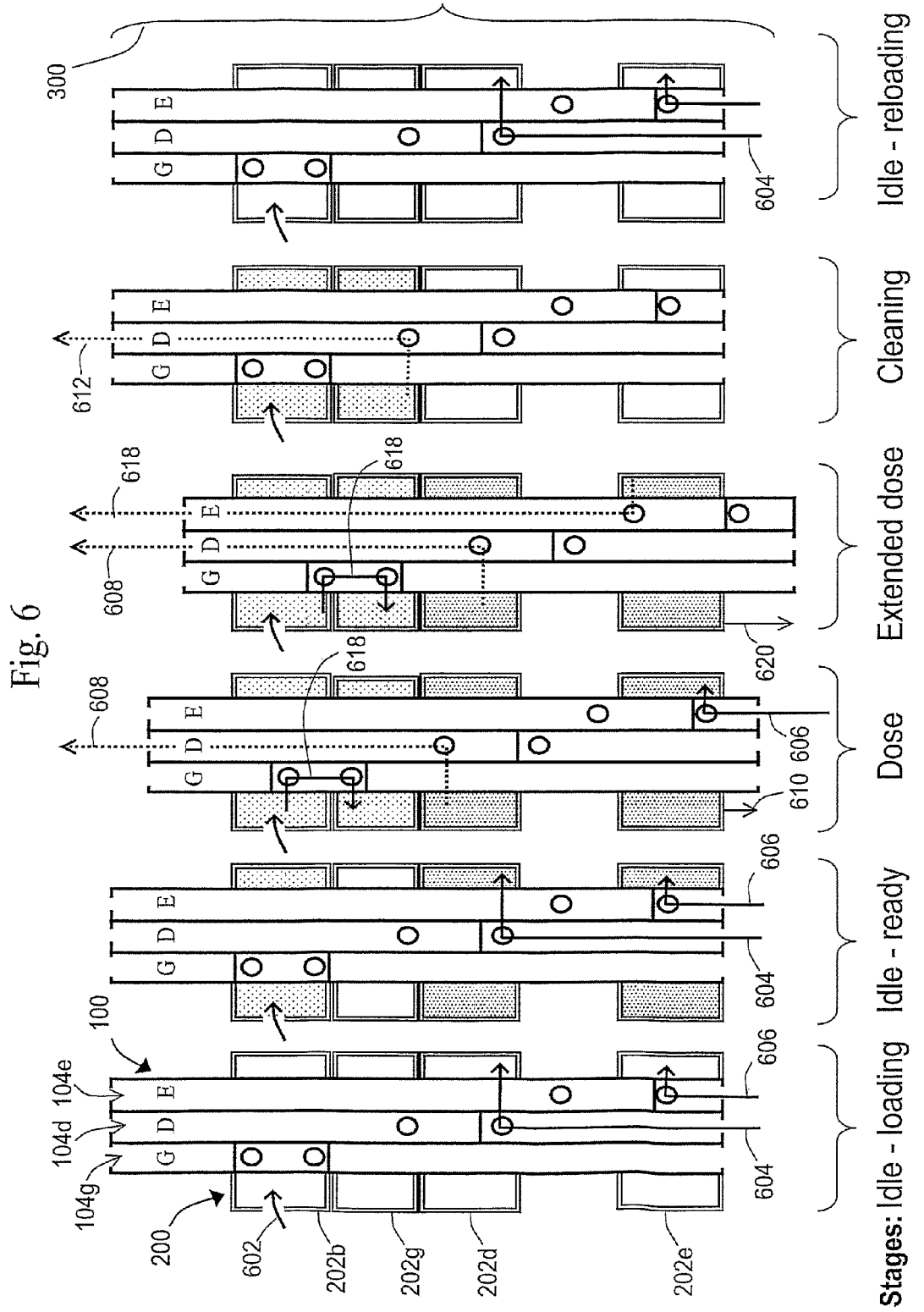
FIG. 6 schematically illustrates some stages in an operation of a triple-lumen stem with an assembly of chambers inside a canister of a fluid propelled by a gas, according to exemplary embodiments of the invention.

For better clarity of the ongoing discussion, the operation of gear 300 in dispenser 400 is described with respect to various schematic positions of stem 100 (or equivalent tubes) inside chambers 202 as exemplary operational stages (or states) which are indicated by tagged brackets therebelow in FIG. 6.

Idle-Loading Stage

Figure 7A:
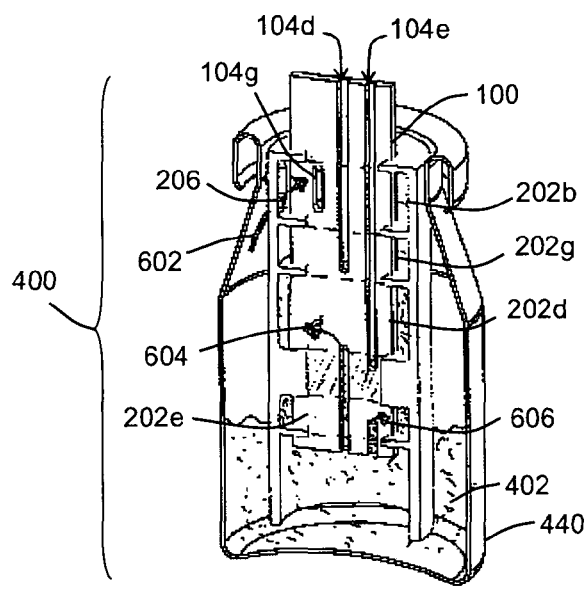
FIGS. 7A-D show cross-sectional depth views of some stages corresponding to stages illustrated in FIG. 6, according to exemplary embodiments of the invention.

Reference is made to 'Idle-loading' section of FIG. 6 and FIG. 7A as an initial idle (not actuated) state where stem 100 is in an idle position relative to chambers 202, and where all chambers 202 of 200 are empty. The state in which all chambers 202 are empty may only be a virtual or instantaneous or transient state, and is used here for clarification of the sequence of operational stages. In practice, in some embodiments, at least some of chambers 202 are in loading (filling) progress as described below.

The idle state of stem 100 is indicated for convenience with the lower edge coinciding or about the lower edge of assembly 200 (e.g. edge of 202*e*), serving as line or plane of reference. It should be noted that stem 100 may extend further below the lower edge of assembly 200 (for example, as in FIG. 4), yet without some structural measures the lower edge of stem 100 may not lie above the lower edge of assembly 200.

Once in an (initial) idle state, gas 406 enters and fills chamber 202*b* through opening 206 therein, as indicated by arrow 602, where chamber 202*b* serves as a buffer for cleaning chamber 202*g* as described below. Concurrently, due to hydrostatic pressure in fluid 402, fluid 402 enters and load (fills) chamber 202*d* via lower hole 108*d* as indicated by an arrow 604, and loads chamber 202*e* via lower hole 108*e* as indicated by an arrow 606.

For proper operation, upper stopper 502*g* prevents gas 406 from discharging out of upper part of lumen 106*g* and lower stopper 502*g* prevents gas 406 from expanding into down towards fluid 402 via lower part of lumen 106*g*. Optionally, upper and lower parts of lumen 106*g* (above and below stoppers 502*g*) are closed or filled (not hollowed), leaving the section between holes 108*g* as actual lumen 108*g*.

Likewise, stoppers 502*d* and 502*e* prevent fluid 402 to thrust further into lumens 104*d* and 104*e*, respectively, and possibly into unintended chambers.

Idle-Ready Stage

Referring to 'Idle-ready' section of FIG. 6, after chamber 202*b* is filled with gas 406 and chambers 202*d* and 202*e* are filled with fluid 402, gear is 300 (or corresponding dispenser 400) is ready for operation of dispensing fluid and post-cleaning.

In some embodiments, the loading stage is sufficiently fast such that idle-loading and idle-ready stages practically coalesce.

It should be noted the fluid 402 loaded into chambers 202*d* and 202*e* is pressurized as it comprises a liquefied or otherwise condensed gas, so that equilibrium of gas-liquid is established in the chambers, or alternatively fluid 402 is under pressure of another gas 406.

Dose Stage

Figure 7B:
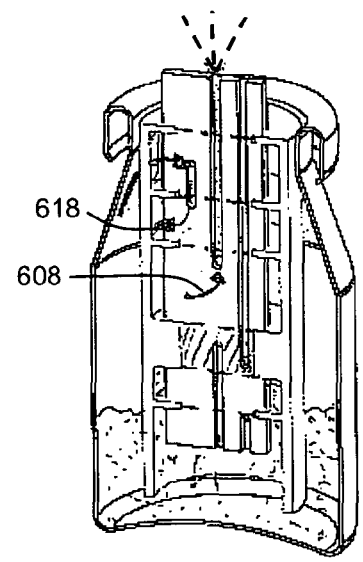

Reference is made to 'Dose' section of FIG. 6 and FIG. 7B, where stem 100 is pushed down from an idle-ready stage, as indicated by an arrow 610 (referred to as 'half-push'). Lower hole 108*d* disconnects the bulk of fluid 402 in canister 400 from chamber 202*d*. Concurrently upper hole 108*d* connects chamber 202*d* with the upper portion of lumen 104*d* (above stopper 502*d*) that is open to the outside environment (e.g. air or any ambient atmosphere). The pressurized gas expands into lumen 104*d* and expels the fluid contents of chamber 202*d* through the upper opening of lumen 104*d*, as indicated by an arrow 608. Since chamber 202*d* is of a known (controlled, preset) volume a metered dose is discharged through lumen 104*d* (hence the 'd' designation).

Concurrently, holes 108*g* move down, providing a bridge (passage) for gas 406 between buffer chamber 202*b* and gas cleaning chamber 202*g*, filling chamber 202*g* as indicated by an arrow 618.

While in the dose stage, chamber 202*e* is still connected with fluid 402 through hole 108*e* as indicated by an arrow 606.

Extended-Dose Stage

Figure 7C:
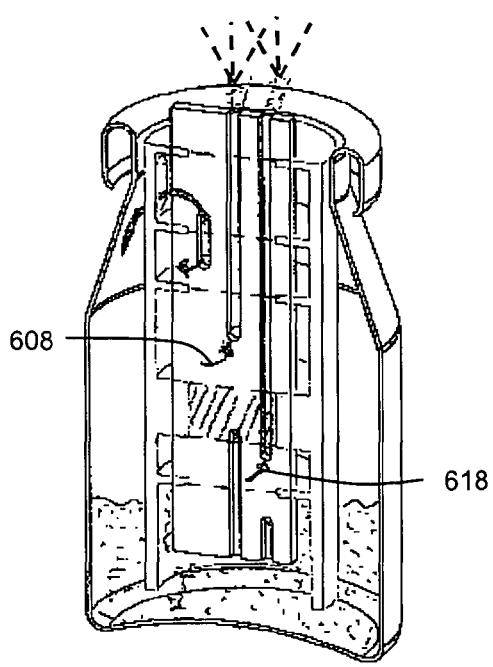

Reference is made to 'Extended dose' section of FIG. 6 and FIG. 7C, where stem 100 is pushed down from an idle-ready stage further than in the dose stage, as indicated by an arrow 620 (referred to as 'full-push'). Lower hole 108*d* disconnects the bulk of fluid 402 in canister 400 from chamber 202*d*, while upper hole 108*d* connects chamber 202*d* (further below that in dose stage) with the upper portion of lumen 104*d* (above stopper 502*d*) that is open to the outside environment.

Concurrently, lower hole 108*e* disconnects the bulk of fluid 402 in canister 400 from chamber 202*e* while upper hole 108*e* connects chamber 202*e* with the upper portion of lumen 104*e* (above stopper 502*e*) that is open to the outside environment.

As both chamber 202*d* and 202*e* are isolated from the fluid bulk and are open to the outside, two metered volumes of fluid are expelled out, one of chamber 202*d* and one of chamber 202*e*, as indicated by arrows 608 and 618, respectively. The combined volume of chamber 202*d* and chamber 202*e* is larger than the volume of chamber 202*d*, such that the contents of chamber 202*e* extends the dose of chamber 202*d* (hence the 'e' designation).

Concurrently, holes 108*g* move further down while still providing a bridge for gas 406 to fill gas cleaning chamber 202*g* from buffer chamber 202*b* as indicated by an arrow 618.

With chambers 202*d* and 202*e* operating by each respective lumen independent of each other (up to the combined operation of stem 100 as described), extended dose of chamber 202e may be discharged concurrently with dose of chamber 202e by pushing stem 100 from an idle ready stage as described above, or as an additional step after discharging the dose of chamber 202d, either fully or partially.

The volumes of chambers 202d and 202e are independent of each other so that by setting or adjusting their respective volumes different metered doses can be discharged.

Cleaning Stage

Figure 7D:
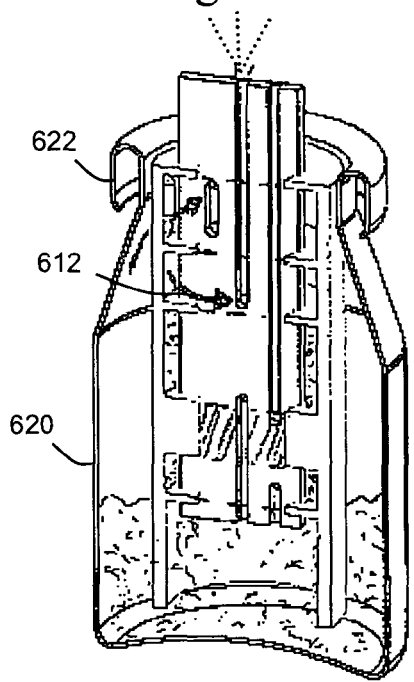

Reference is made to 'Cleaning' section of FIG. 6 and FIG. 7D, where stem 100 is pulled up back to an idle position (either after a dose or extended dose were released). The bridge between gas buffer chamber 202b and cleaning chamber 202g is disconnected (both ends are within chamber 202b), while upper hole 108d (above stopper 502d) connects gas cleaning chamber 202g to the outside environment via upper portion of lumen 104d, letting gas 406 expand and expel out of chamber 202g.

As chamber 202b is always open to canister 440 via opening 206, chamber 202b always maintains (buffers) a volume of gas for gas discharge from chamber 202g (hence the 'b' and 'g' designations, respectively).

Since gas 406 is expelled after does or extended dose were discharged, gas 406 cleans a nozzle or other outlet (not shown) used for dispensing fluid 402.

It should be observed that post-cleaning is enabled by a preceding dispensing of one or more doses since chamber 202g is loaded responsive to moving stem 100 down for dispensing a dose.

Idle-Reloading Stage

Once stem 300 is in an idle position, chambers 202d and 202e re-load as described above ('Idle-loading' stage) until gear 300 is ready for another dose discharge.

In some embodiments, the cleaning stage and loading stage are concurrent, at least partially.

When only chamber 202d was released in a preceding operation, chamber 202e is still loaded and is in connection with the bulk of fluid 402.

Some Variations

Referring to FIGS. 6 and 7A-D (and with respect to FIGS. 1-5), some variations may be observed or concluded, as briefly exemplified below.

In some embodiments of the invention, eliminating chambers 202b and 202g as well as lumen 104g from gear 300, the resulting structure can be used to dispense two different metered doses without post-cleaning.

If gear 300 is further reduced to eliminate chamber 202e and lumen 104e, then the resulting structure can used to dispense one metered dose according to chamber 202d.

In some embodiments of the invention, gear 300 comprises more than two fluid chambers. The positions of chambers 202 in assembly 200 and stem 100 structure (e.g. number and positions of holes 108 and stoppers 502) are adapted to discharge particular dose or doses such as 1-3 metered doses.

On the other hand, gear 300 may be modified to maintain only the cleaning or post-cleaning structures. For example, maintaining chambers 202b and 202g and upper part of lumen 104g and discharging cleaner effluent responsive to an actuation such as pushing and releasing lumen 104g for dispensing a fluid (e.g. fluid 402). Optionally, a dose is dispensed by another mechanism, such as a pump.

In some embodiments, the cleaning mechanism comprises more than two chambers, such as a pair for each dose chamber or for dispensing different cleaners (such as if one is not suitable) and/or for alternating between fluid dose discharges.

In some embodiments, buffer chamber 202b may be eliminated and chamber 202g is loaded from the gas phase in a volume of a section of canister 440 (e.g. through a one-way valve) or from a separate can (inside or outside of canister 440) containing a volume finable or filled with cleaning effluent.

In some embodiments, chambers 202 in assembly 200 form a plurality of hollow passages such as passage 204 and one or more tubes (or stems) move in the respective passages, preferably in concerted movement. Optionally, chambers 202 do not form a passage 204 and tubes or stems or stems move alongside the walls of the chambers which have valves openings to match the openings in the tubes or lumens of the stems. Optionally or alternatively, a combination of internal passage and wall-side openings is used.

In some embodiments of the invention, instead of an upper part and lower part of a lumen (e.g. upper parts of lumen 104d above and below stopper 502d) two separate tubes or lumens are used.

In some embodiments, other variations may be used such as packing (bundling) tubes in one or more groups or having a plurality of rods with different lumens, or forming a portion or a part of the tubes as a lumen or lumens in one or more stems.

In some embodiments of the invention, the pressure on fluid 402 is applied by providing a pressurized gas 406 which is not a gaseous phase of fluid 402. For example, compressing air by a pump such as a part of actuating the dispenser (see below), or by providing a can with pressurized gas.

Actuating

In some embodiments of the invention, gear 300 is maintained in an idle position by an elastic element and/or mechanism. To actuate gear 300, stem 100 is pushed against the force of the elastic element and/or mechanism from the idle position by half-push or full-push to discharge a dose or extended dose, as described above (e.g. FIGS. 7B and 7C, respectively). As the pressure (push) on stem 100 is released, the elastic element and/or mechanism urges stem 100 back to the idle position.

Figure 8A:
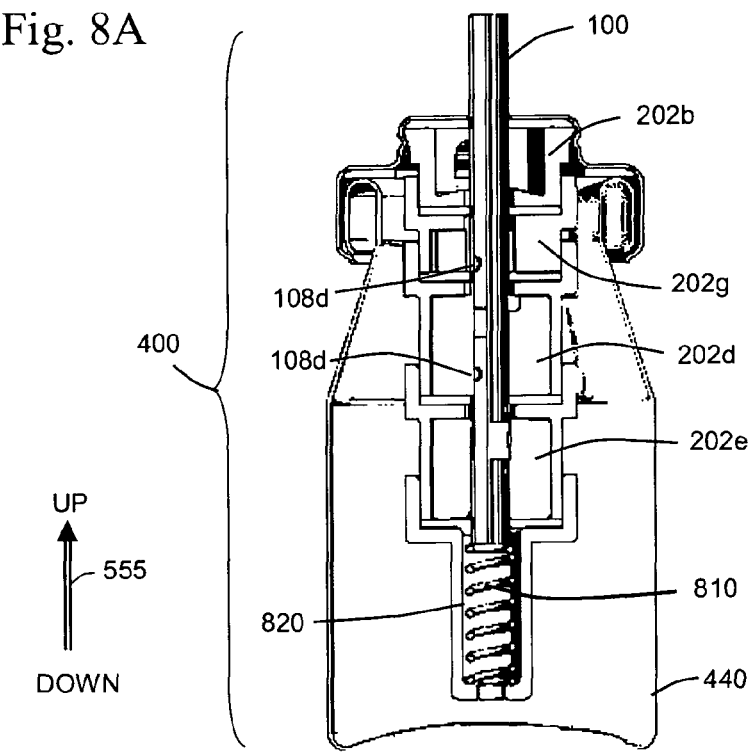
FIGS. 8A-C schematically illustrate an assembly of a stem and chambers disposed in a dispenser, where the stem is linked to a spring in three activation stages, according to exemplary embodiments of the invention.
Figure 8B:
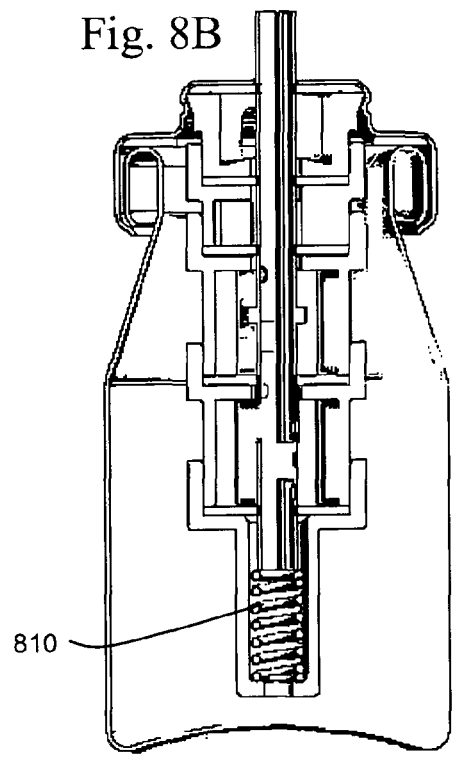
Figure 8C:
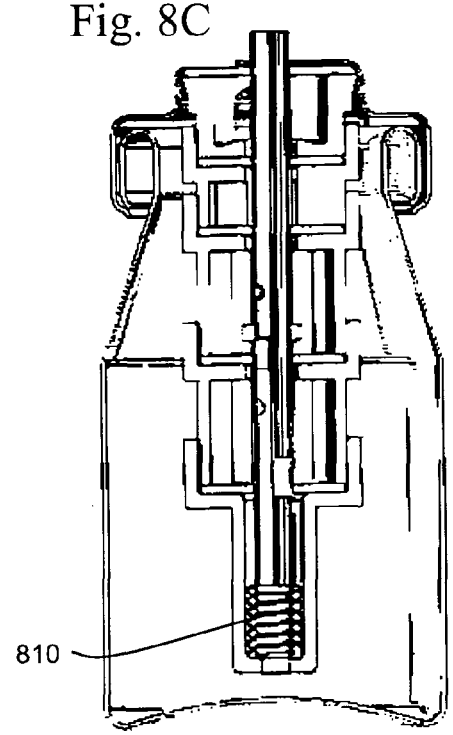

FIGS. 8A-C schematically illustrate an assembly of stem 100 and chambers 202 disposed in dispenser 400 (canister 440), where stem 100 is linked to a spring 810 in three activation stages, according to exemplary embodiments of the invention.

FIG. 8A shows dispenser 400 comprising canister 440 in which stem 100 is inserted in chambers 202b, 202g, 202d and 202e (assembly 200) and positioned on (linked to) spring 810 disposed in a hollow 820. The dispenser is in idle state and spring 810 impels stem 100 upwards, where arrow 555 indicates an up direction (at least approximately).

FIGS. 8B and 8C show dispenser 400 in half-push state (dose stage) and full-push (extended dose), respectfully, where in FIG. 8C spring 810 is maximally pressed (with respect to dispenser 400), wherein in FIG. 8B spring 810 is in an intermediate state between the full-push state and the idle state.

In some embodiments, instead of spring 810 another element or elements or mechanism may be used, for example, a resilient band, or a piston linked to stem 100 which compresses a gas in a cylinder as it is pushed down, or a tapered hollow which widens as stem 100 is pushed down.

In some embodiments, stem 100 is attached or connected to an actuator, optionally together with or linked with element or elements or mechanism as described above with respect to spring 810. The actuator may be any element and/or mechanism that by applying an external force (e.g. by finger, hand or a moving part on a machine) moves stem 100 from an idle state into a half-push of full-push states, such as a button, handle or a trigger. In some embodiments, the actuator is a nozzle connected on stem 100 (see also below).

In some embodiments of the invention, the controlled doses are dispensed by similar stepwise activations of the very same actuator. For example, as typically found in many dispensers, the actuator is a button about the top of the dispenser, which is pressed downwards against some force in order to discharge a fluid via an outlet. In some embodiments of the invention, pressing the button some way downwards releases a pre-set dose from a chamber, and pressing the button further down, optionally with greater force, releases another pre-set dose from another chamber. The operation may be continued in a similar stepwise manner releasing successive doses according to the number of chambers. Optionally or alternatively, the operation may be repeated, optionally partially, after the actuator is released to dispense a particular dose or doses.

In some embodiments, dispenser 400 and/or chambers 202 provide structures that limit and/or constrict stem 100 into particular positions for idle, dose and extended dose states, preventing stem 100 from being loosely disposed in chambers assembly 200 and/or dispenser 400.

In some embodiments, a tactile and/or audible feedback is provided for each actuation step, optionally somewhat impeding the activation between steps, providing better operational control and/or reliability. For example, providing an audible and/or tactile 'click' response for each state such as by protrusion or protrusions on edges of passage 204 that push into recesses on stem 100 as stem 100 moves into particular positions (states).

Figure 9:
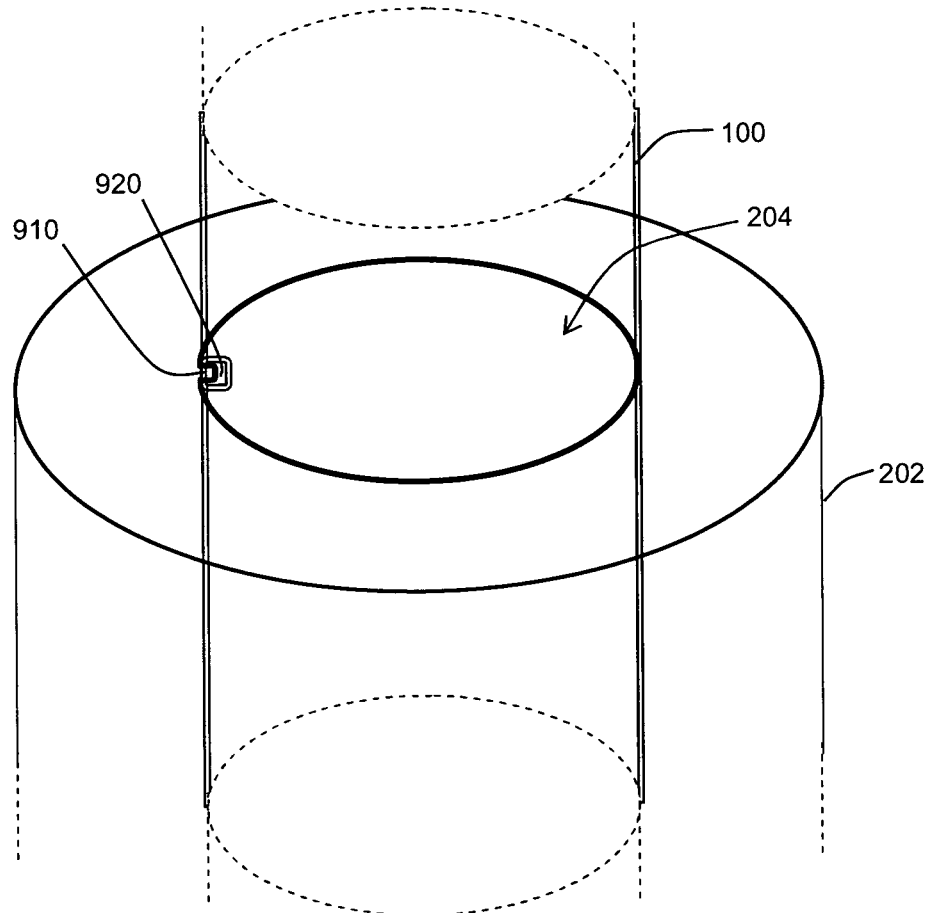
FIG. 9 schematically illustrates structures for constricting a position of a stem moving in a chamber passage, according to exemplary embodiments of the invention.

FIG. 9, with further reference to FIGS. 1-3, schematically illustrates structures for constricting a position of stem moving in a chamber passage, according to exemplary embodiments of the invention. A chamber 202 (all or some of chambers 202) has a protrusion 910 into passage 204, where the protrusion has some flexibility and/or elasticity (or is part of a mechanism such as ball with a spring). Stem 100 has a recess 920 according to a particular state with respect to chambers 202 (e.g. half-push). As stem 100 moves in passage 204 (moving over protrusion 910), when a particular position of a step is reached, protrusion 910 flips into recess 920, impeding or stopping or halting stem 100 in the specific respective state. Stem 100 is halted at least momentarily or under a resistance somewhat larger than of a typical actuation or of an intermediate position between states, or as a 'click' as known in the art.

In some embodiments, other or additional methods and/or mechanisms are used to actuate a particular dose and/or maintain a state such as an idle state. For example, the actuator or an attached or a connected structure, for example a nozzle or a flange, is placed above recesses of different depth so that the actuator is moved down to a recess bottom, while the idle state is maintained by a mechanism such as spring 810 or by placing the nozzle (or flange) over a bridge between the recesses. Optionally, a recess and/or another structure of mechanism may be used to lock the nozzle to prevent inadvertent actuation (safety lock).

Figure 10:
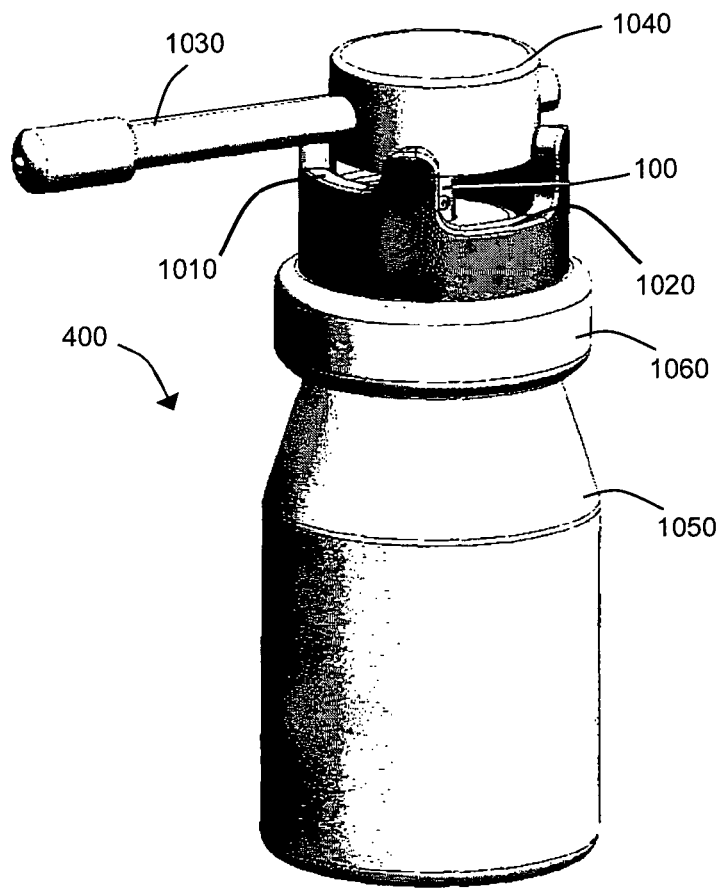
FIG. 10 schematically illustrates a dispenser comprising a nozzle as a spout rotatably locatable over a plurality of recesses, according to exemplary embodiments of the invention.

FIG. 10, with further reference to FIGS. 1-4, schematically illustrates a dispenser 400 comprising a nozzle 1030 as a spout rotatably locatable over a plurality of recesses 1010 and 1020, according to exemplary embodiments of the invention. Spout (nozzle) 1030 is connected to stem 100 via a knob 1040 wherein dispenser 400 in an idle state as illustrated. When spout 1030 is rotated over recess 1010, the recess allows actuating (pressing) stem 100 only for a distance for halfpush (dose dispensing), and when spout 1030 is rotated over recess 1020, the recess allows and controls actuating (pressing) stem 100 only for a distance for full-push (extended dose dispensing). In some embodiments, other methods such as described above may be combined with the recess method for controlling the pushing distance, such providing a 'click' mechanism.

Structure

Respective to the discussion above and FIGS. 1-8, chambers 202 can have any shape, provided that the chambers are arranged (such as in assembly 200) such that stem 100 holes connect or disconnect with the chambers to enable operation of dispenser 400 as exemplified above.

In some embodiments of the invention, chambers 202 are constructed from parts assembled one on top the other. Optionally, the parts are modular. In some embodiments, the middle parts or all the parts are manufactured as identical parts and adjusted (trimmed) for particular chambers volume.

Figure 11:
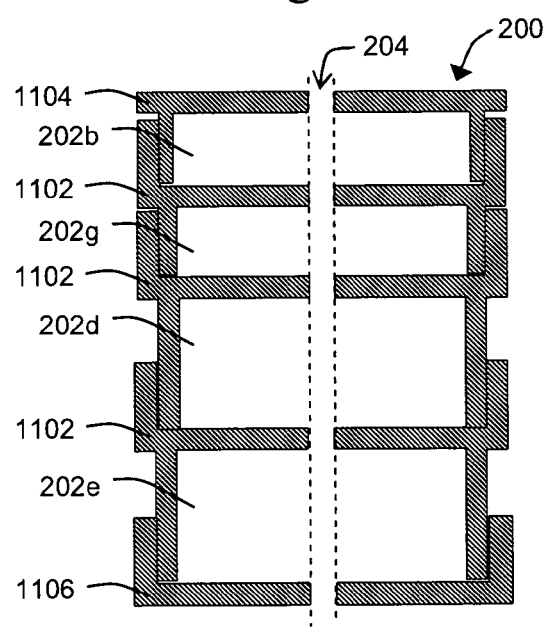
FIG. 11 schematically illustrates an assembly of chambers made of modular parts where the intermediate parts have similar shape, according to exemplary embodiments of the invention.

FIG. 11, with respect to FIGS. 1-4, schematically illustrates assembly 200 of chambers 202 made of modular parts forming passage 204 therebetween where the intermediate parts 1102 have similar shape, according to exemplary embodiments of the invention. Such a structure is also illustrated in FIGS. 7-8. Optionally, top part 1104 and bottom part 1106 have similar shape, which may simplify production and assembly of assembly 200. Optionally, bottom part 1106 is elongated to provide room for a mechanism participating in actuation of dispenser 400, for example, as illustrated by hollow 820 housing spring 810 in FIG. 8. Optionally or additionally, top part 1104 (and/or other parts) comprise element and/or mechanism for restriction of stem 100 in particular states as exemplified by protrusion 910 and recess 920 in FIG. 9.

In some embodiments of the invention, all or some of parts of assembly 200 and/or stem 100 are made of plastic (e.g. polymeric) material, optionally with additional ingredients for properties such as strength or resistance to chemicals in canister 440. Optionally, all or some of parts of assembly 200 and/or stem 100 are made of other materials, such as metal, composite materials or a combination of a plurality of materials. For example, referring to FIG. 5, stem 100 may comprise adjoined tubes extruded from some polymeric material and assembled with stoppers 502 made of metal or another material.

In some embodiments of the invention, gear 300 (assembly 200 of chambers 202 and stem 100 inserted in passage 204) is disposed in canister 440, where canister 440 is shaped like a bottle or as a can of other shape which is closed by a lid, as exemplified by a bottle 1050 and a lid 1060 in FIG. 10. Typically, the lid is formed with a passage for stem 100 or an extension thereof or for an element or a mechanism attached or linked to stem 100.

In some embodiments, bottle such as 1050 and lid such as 1060 are manufactured particularly for dispenser 400. Optionally or alternatively, the bottle is commercially available where the lid is manufactured particularly for dispenser 400 or a commercially available lid is modified. Optionally, a commercially available design is modified to fit to dispenser 400 and manufactured accordingly.

In some embodiments, dispenser 400 comprises an outlet, such as a nozzle. Optionally, the nozzle is connected to stem 100 or linked to stem 100 by intermediate element or elements such as an extension of stem 100 or a tube that connects lumens 104$d$ and 104$e$ (optionally also lumen 104$g$) to the nozzle. Referring to FIG. 10, for example, stem 100 is connected via knob 1040 having one or more conduits therein that collect the discharge from lumens 104$d$ and 104$e$ and direct the discharge into nozzle 1030.

Ingredients and Applications

Referring to FIG. 4 as an example, in some embodiments of the invention, fluid 402 is a condensed phase of gas 406 wherein gas 406 serves as propellant. In some embodiments, fluid 402 comprises other ingredients in a dissolved or suspension or emulsion form, such as one or more lubricants, surfactants, viscosity and/or elasticity agents, medications, reagents (that react once disposed to the outside environment).

In some embodiments of the invention, the fluid, such as fluid 402, is discharged as a flow of liquid, gas, spray, foam, solution, suspension, emulsion, gel, colloid, powder, microparticles, cream, lotion or paste form, or a combination thereof, optionally in combination of a gas such as gas 406. Optionally, due to the substance of the fluid or ingredients therein, the dispensed fluid hardens or thickens or solidifies to some extent, forming into a phase such as a paste or soft solid or hard solid.

In some embodiments, once fluid 402 enclosed in a chamber with gas 406 phase (e.g. in equilibrium) is discharged from the chamber (e.g. chamber 202*d*), the expanding gas form bubbles in the fluid such that the fluid is dispensed out of the outlet (e.g. nozzle) as foam (which denotes also a froth or lather). In some embodiments, the substance of the dispensed fluid or ingredients therein, causes the foam to harden or solidify or congeal to some extent, forming a phase such as a solid or semi-solid or a soft substance, for example, a gel or a gas-solid or gas-liquid colloid. Optionally, the fluid is dispensed as a fluid spray, which may optionally congeal into forms such as suspension or aerosol. In some embodiments, the phase changes as described above result, at least partly, due the evaporation of the gas and/or fluid in the outside environment.

In some embodiments of the invention, ingredients in fluid 402 comprise dissolved material or materials such as pharmaceutically active ingredients. Optionally, the ingredients comprise distinct phase in the fluid phase such as solid powder suspension or liquid particles emulsion. Optionally or alternatively, the fluid comprises, at least to a significant extent, a solid phase such as powder.

In some embodiments of the invention, fluid 402 comprises medications which have to be dispensed in controlled volumes or quantities. For example, applying controlled quantities of ear medication which forms into a foam in the ear structure keeping the medication intact and/or isolating the ailing ear from outside infections, optionally providing a slow release of the medication into the ear interior. Another example is applying medication in controlled volume into locations such as eye, nose, vagina, rectum, mouth or any other body cavity, body part or body such as the skin (usually named as topical formulation) or for inhalation (directly or by employing inhalation apparatus).

In some embodiments, fluid 402 comprises lubricants which have to be dispensed in controlled volumes or quantities on appliances such as fine machinery (e.g. gages, watches), where in some cases the gas evaporates leaving the lubricant on the appliance.

In some embodiments, fluid 402 comprises adhesives which have to be dispensed in controlled volumes or quantities on appliances or in surgery, where in some cases the gas evaporates leaving the adhesive on the appliance or organ.

In some embodiments, the cleaning gas is the same as a propellant gas such as gas 406. Optionally in some embodiments, the cleaning gas is a different gas (e.g. when gas 406 is not suitable for cleaning). In some embodiments, the cleaning gas is provided separately in a can or chamber which connects to gas buffer chamber 202*b* such as via opening 206. The cleaning gas may be placed inside canister 440 outside of canister 440, such as in auxiliary can connected by an auxiliary tube.

In some embodiments of the invention, a fluid such as a liquid is used for post-cleaning (e.g. when dispensed fluid residue has to be dissolved). For example, the cleaning liquid is held in a gas pressurized can disposed inside canister 440 and the cleaning liquid is operated in chamber 202*b* and 202*g* in a similar manner as gas 406.

In some embodiments, the cleaning fluid is used to react with the dispensed material or with a modification thereof (e.g. in a colloid form), such as to provide a polymerization catalyst (akin to epoxy glue operation) to the preceding dose. In some embodiments, the cleaning fluid is used to react with the dispensed substance or a modified form thereof, thereby effecting removal, inactivation or disintegration thereof, optionally, the reaction is used for facilitating removal of residues in an outlet such as a nozzle.

In some embodiments of the invention, fluid 402 is not a condensed phase of propellant gas 406, and may have low vapor pressure in canister 440 such that the vapor pressure is not sufficient to propel fluid 402 out of dispenser 400. Optionally, such fluid 402 is pushed out of chamber (e.g. chamber 202*d* or 202*e*) by having a connection between the chamber and propellant gas 406. For example, a one-way valve or valves that allows the gas to push fluid 402 out of a chamber into a dispensing lumen (i.e. that connects outside) but not back into canister 440, while optionally blocking gas 406 from entering the chamber once it is empty of fluid 402 such as by a valve under some force that allows the gas to push into a chamber only when the chamber is open to the outside environment (e.g. via a lumen).

While various substances may be used as propellant and/or dispensed (i.e. expelled) compositions, in some particular embodiments of the invention the substances are in a fluid form either as gas and/or liquid or combination thereof, while in some specific embodiments the same substance is used for propulsion (pressure) and dispensing.

Providing the discussions and examples above, a person skilled in the art would gather other structures, ingredients and applications.

Kit

Referring to FIGS. 1-5 and FIG. 11, in some embodiments of the invention gear 300 is provided either as assembled gear 300, or as chambers assembly 200 and stem 100, or as partially assembled assembly 200 and/or partially constructed stem 100, or in parts of assembly 200 and/or stem 100.

In some embodiments, stem 100 is provided as parts thereof, optionally suitable to form a stem to operate according to the number and type (dose/cleaning) of chambers.

In some embodiments, the parts of gear 300 are provided as a kit, optionally comprising assembling and usage instructions, for example, for assembling and installing gear 300 in a can or bottle (e.g. ear medicine bottle), as described above.

Figure 12A:
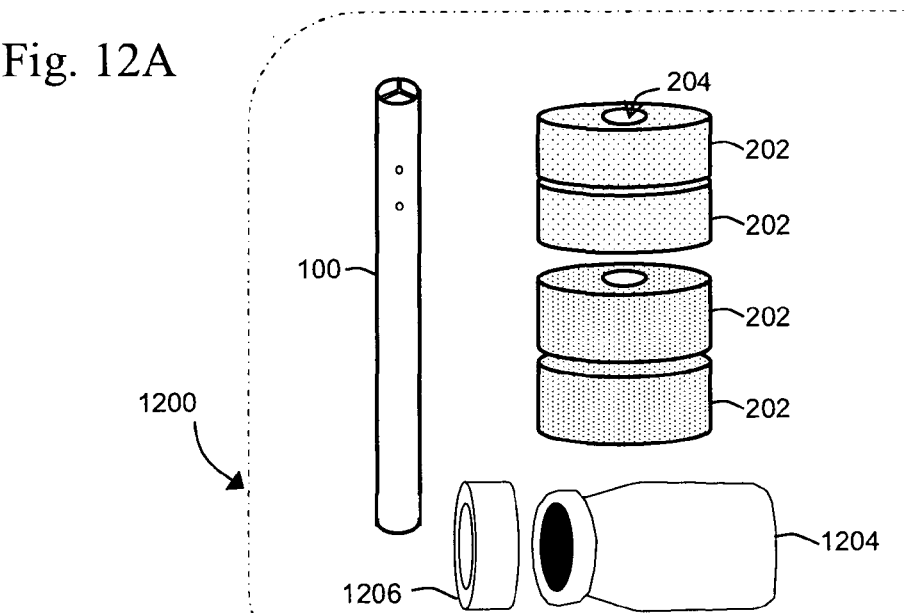
FIG. 12A schematically illustrates a kit comprising chambers, a stem and a can with a corresponding cap, according to exemplary embodiments of the invention.

FIG. 12A schematically illustrates a kit 1200 comprising chambers 202, stem 100 and a can 1204 (such as canister 440) with a corresponding cap 1206, according to exemplary embodiments of the invention.

Figure 12B:
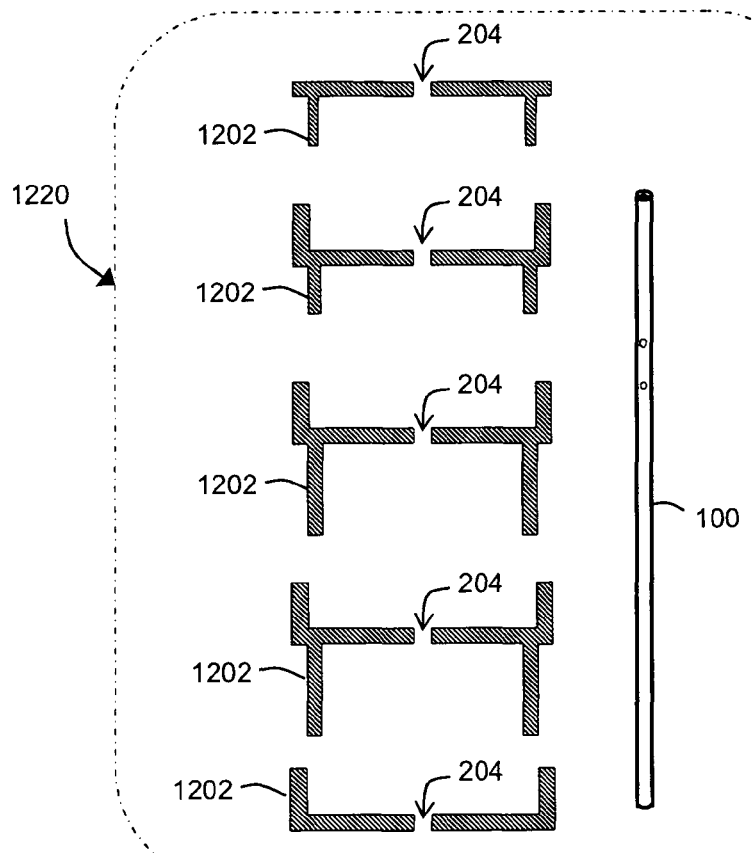
FIG. 12B schematically illustrates a kit comprising chambers parts and a stem, according to exemplary embodiments of the invention.

FIG. 12B schematically illustrates a kit 1220 comprising chambers parts 1202 (similar to parts 1102-1106 of FIG. 11) and stem 100. Parts 1202 can be assembled to form dose chambers for metered dose dispensing and/or to form chambers for cleaning fluid, for example, as described with respect to FIG. 11.

In some embodiments, a combination of chambers and chambers parts are provided for assembly into an assembly such as assembly 200. In some embodiments, stem 100 is provided inside passage 204 as gear 300. In some embodiments, kit 1200 or 1220 comprises components for a plurality of gears 300.

It should be noted that stem 100 represents any combination of lumens or tubes, as discussed above, and chambers 202 (or parts 1202) may form any number of chambers (as practical or required) to operate with the lumens or tubes as discussed above.

In some embodiments of the invention, the kit, such as kit 1200 or kit 1220, further comprises a canister (e.g. canister 440) as illustrated by can 1204 and optional auxiliary components such as cap 1206. By providing gear 300 (assembled or as parts thereof) and a canister, a dispenser (e.g. dispenser 400) may be assembled. The dispenser may be filled with a fluid (e.g. fluid 402) and/or a propellant (e.g. gas 406) and/or a cleaning fluid (e.g. for reacting with residues of fluid 402).

In some embodiments of the invention, fluid such as 402 and gas such as gas 406 are provided in a kit. For example, by a cylinder storing a compressed and liquefied gas. Optionally or alternatively, the fluid and propellant and/or cleaning effluent are provided separately in a kit.

In some embodiments, the kit such as kit 1200 or kit 1220 comprise auxiliary elements such as sealing elements (e.g. o-ring or o-rings) and/or materials (e.g. sealant) and/or tools to assemble gear 300 or a dispenser or part thereof. Optionally, a user guide or manual is provided to guide or assist in assembling the dispenser.

It should be noted that the kits as illustrated in kit 1200 and kit 1220 are provided as examples and represent other variations of components such as a kit including only chambers 202*b*, 202*g*, 202*d*, 202*e* and stem 100 and assembling instructions, or a kit comprising assembly 200 of chambers 202 and a plurality of tubes.

Method

FIG. 13 schematically illustrates a flowchart outlining actions for dispensing a plurality of metered doses of a fluid with optional cleaning, according to exemplary embodiments of the invention.

The fluid is provided in a container comprising a plurality of chambers and a plurality of tubes connectable to and movable relative to the chambers, wherein the tubes are externally open or opened to the fluid (1302).

In some embodiments, with respect to FIG. 4, the container is represented by canister 440 and the fluid is represented by fluid 402 and the chambers are represented by chambers 202, and with respect to FIG. 5, the tubes are represented by lumens 104*d* and 104*e*.

In some embodiments, the tubes are movable in a passage formed by the chambers and connect to the chambers by holes formed on sides of the tubes. Optionally and preferably, the positions of the holes are planned for synchronized (concerted) operation of the tubes with respect to the chambers and fluid.

In order to prepare the required amounts of doses (metering), tubes opened to the fluid are connected to the chambers, thereby loading the chambers with metered amounts of fluid (1304).

Typically and preferably, when a chamber loads with fluid, and before dispensing, the chamber is cut off from the external environment.

In order to dispense a dose or a plurality of doses, one or more externally open tubes are selectively connected to one particular chamber or to a plurality of particular chambers loaded with fluid, thereby dispensing the metered fluid contents of the one particular chamber or the plurality of the particular chambers via the externally open tubes (1306). In some embodiments, dispensing the contents of the plurality of particular chambers comprises a simultaneous dispensing of the combined metered contents of the plurality of the particular chambers.

Typically and preferably, when dispensing a dose from a particular chamber, that particular chamber is cut off from the fluid.

In some embodiments of the invention, the container comprises an outlet in which undesirable residues of the dispensed fluid may accumulate, clogging the outlet or having other adverse effects, such as transforming into a harmful compound.

Therefore, in some embodiments of the invention, the container is provided with a cleaning effluent at least one additional chamber and an additional movable tube opened to the cleaning effluent (1308). The term 'effluent' is used to differentiate the cleaning fluid from the dispensed fluid, although in some embodiments both the dispensed fluid and the cleaning fluid are substantially or basically the same substance, such as when the dispensed fluid is substantially a condensed form (e.g. liquefied) of the cleaning fluid (effluent), so that, for example, when opening to the external environment the liquid propellant is altered to a gas.

The additional chamber is connected to the tube opened to the cleaning effluent, thereby loading the additional chamber with cleaning effluent (1310).

In order to release the cleaning effluent, an externally open tube is connected to the additional chamber loaded with cleaning effluent, thereby dispensing the cleaning effluent via the externally open tube (1312) to the outlet.

Typically and preferably, dispensing the cleaning effluent is enabled and/or facilitated only subsequent to dispensing the one or more metered dose as described above.

The invention claimed is:

1. A method for dispensing a plurality of metered doses of fluid by a dispenser, comprising:
   (a) providing a fluid in a container comprising a plurality of metering chambers and a plurality of tubes connectable to and movable relative to the chambers;
   (b) connecting to the chambers tubes open to the fluid, thereby loading the chambers with fluid;
   (c) selectively connecting one or more externally open tubes to one or more chambers, thereby dispensing the fluid contents of the one or more chambers via an external opening;
   (d) providing in the container a cleaning effluent, at least one additional chamber and an additional movable tube open to the cleaning effluent;
   (e) connecting to the additional chamber the tube open to the cleaning effluent, thereby loading the additional chamber with cleaning effluent; and
   (f) connecting an externally open tube to the additional chamber, thereby dispensing the cleaning effluent via the externally open tube.

2. The method according to claim 1, wherein connectable to the chambers comprises having holes at planned positions on the tubes, selectively providing or preventing a passage between a tube and a chamber.

3. The method according to claim 1, wherein selectively connecting comprises moving tubes to a position where a particular chamber is connected to an externally open tube while concurrently disconnecting the particular chamber from a tube open to the fluid.

4. The method according to claim 1, wherein selectively connecting comprises moving tubes to a position where particular chambers are connected to externally open tubes while concurrently disconnecting the particular chambers from tubes open to the fluid.

5. The method according to claim 1, wherein selectively connecting comprises progressively moving tubes to consecutive positions, successively connecting particular chambers to externally open tubes while disconnecting the particular chambers from tubes open to the fluid.

6. The method according to claim 1, wherein dispensing the fluid contents comprises at least one of a liquid, gas, spray, foam, solution, suspension, aerosol, emulsion, gel, colloid, powder, microparticles, cream, lotion or paste form, or a combination thereof.

7. The method according to claim 1, wherein providing a fluid in a container comprises providing a fluid pressurized by a pressure greater than the ambient pressure outside the container.

8. The method according to claim 1, wherein connecting externally open tube to the additional chamber comprises moving tubes to a position where the additional chamber is connected to an externally open tube while synchronously disconnecting the additional chamber from the tube open to the cleaning effluent.

9. The method according to claim 1, wherein connecting externally open tube to the additional chamber is facilitated subsequently to dispensing a fluid from at least one other chamber.

10. The method according to claim 1, wherein a tube open to the cleaning effluent comprises a tube connected to a further provided auxiliary chamber open to the cleaning effluent.

11. The method according to claim 1, wherein providing an effluent comprises providing a gas at a pressure greater than the ambient pressure outside the container.

12. The method according to claim 1, wherein providing an effluent comprises providing a fluid alterable to a cleaning effluent.

13. An dispenser apparatus for dispensing a plurality of metered doses of fluid, comprising:
  (a) a container fillable with a fluid to at least a portion of the container;
  (b) a plurality of chambers disposed in the container;
  (c) a plurality of tubes open to said portion, connectable to and movable relative to the chambers, providing selectable connections between said portion and the chambers for loading the fluid to the chambers; and
  (d) a plurality of externally open tubes connectable to and movable relative to the chambers, providing a selectable external connection to at least one chamber for dispensing the content of the at least one chamber;
  (e) at least one additional chamber, disposed in the container, connectable to an externally open tube; and
  (f) at least one additional tube, open to the container outside of said portion, connectable to and movable relative to the additional chamber and allowing a selectable connection between the additional chamber and outside of said portion for loading into the additional chamber a provided cleaning effluent for a subsequent discharge via the externally open tube.

14. The apparatus according to claim 13, wherein connectable to the chambers comprises having holes at planned positions on the tubes, selectively providing or preventing a passage between a tube and a chamber.

15. The apparatus according to claim 13, structured to effect a mutual exclusiveness of (i) providing connections between said portion and the chambers and (ii) providing an external connection to at least one chamber.

16. The apparatus according to claim 15, wherein structured to effect a mutual exclusiveness comprises at least one tube separated by an internal stopper providing at one side thereof a connection between said portion and the chambers and at another side thereof an external connection to at least one chamber.

17. The apparatus according to claim 13, wherein the cleaning effluent is fillable from outside of said portion.

18. The apparatus according to claim 13, wherein at least a portion of the tubes are packed into a group.

19. The apparatus according to claim 13, wherein at least a portion of the tubes are formed as lumens in a stem.

20. The apparatus according to claim 13, wherein the externally open tubes are connected to an outlet.

* * * * *